United States Patent [19]

Kamen et al.

[11] Patent Number: 5,211,201
[45] Date of Patent: May 18, 1993

[54] INTRAVENOUS FLUID DELIVERY SYSTEM WITH AIR ELIMINATION

[75] Inventors: Dean L. Kamen, Bedford; Valentine Faust, Bow, both of N.H.

[73] Assignee: Deka Products Limited Partnership, Manchester, N.H.

[21] Appl. No.: 792,483

[22] Filed: Nov. 15, 1991

Related U.S. Application Data

[63] Continuation-in-part of Ser. No. 748,341, Aug. 22, 1991, Pat. No. 5,116,021, Ser. No. 615,612, Nov. 19, 1990, abandoned, Ser. No. 673,834, Mar. 22, 1991, Ser. No. 674,813, Mar. 22, 1991, and Ser. No. 614,806, Nov. 19, 1990, each is a continuation-in-part of Ser. No. 523,801, May 15, 1990, Pat. No. 5,088,515, and Ser. No. 345,387, May 1, 1989, Pat. No. 4,976,162, which is a continuation-in-part of Ser. No. 92,481, Sep. 3, 1987, Pat. No. 4,826,482, which is a continuation-in-part of Ser. No. 22,167, Mar. 5, 1987, Pat. No. 4,808,161, and Ser. No. 836,023, Mar. 4, 1986, Pat. No. 4,778,451.

[51] Int. Cl.$^5$ .............................................. A61M 35/00
[52] U.S. Cl. ........................................ 137/1; 137/183; 604/123
[58] Field of Search .................. 604/122, 123, 127; 137/1, 173, 174, 183, 202, 192

[56] References Cited

U.S. PATENT DOCUMENTS

| | | | |
|---|---|---|---|
| 2,252,687 | 8/1941 | Bassett | 137/174 X |
| 3,042,038 | 7/1962 | Beacham | 137/174 X |
| 4,661,097 | 4/1987 | Fischell | 604/123 |
| 4,734,269 | 3/1988 | Clarke | 604/122 X |
| 4,764,166 | 8/1988 | Spani | 604/122 X |
| 4,874,359 | 10/1989 | White | 604/122 X |
| 5,061,241 | 10/1991 | Stephens | 604/122 X |

*Primary Examiner*—Alan Cohan
*Attorney, Agent, or Firm*—Bromberg & Sunstein

[57] ABSTRACT

An air elimination system is provided for an intravenous fluid delivery system for intravenous injection of fluid into a patient. An air-detection apparatus (5) is disposed in an intravenous fluid line (3). A return line (8) is attached to a point in the line (3) below the air-detection apparatus (5). The other end of the return line (8) is attached to a chamber (1, 2, 12) where air may be separated from the fluid. The separation chamber may be a drip chamber (12), a metering chamber (2) or the intravenous supply (1). When air is detected, a valve (11) or valves (7, 9) are switched, so that the intravenous fluid is prevented from flowing to the patient, and so that, when a pump (4) is turned on, the fluid is pumped through the return line (8) to the separation chamber (1, 2, 12).

14 Claims, 3 Drawing Sheets

INTRAVENOUS FLUID DELIVERY SYSTEM WITH AIR ELIMINATION

This application is a continuation-in-part of application Ser. No. 748,341 filed Aug. 22, 1991, now U.S. Pat. No. 5,116,021 (for Quick Disconnect Valve), application Ser. No. 615,612 filed Nov. 19, 1990 now abandoned, (for Acoustic Volume Measurement with Fluid Management Capability), application Ser. No. 673,784 filed Mar. 22, 1991 (for Membrane-Based Rotary Peristaltic Pump), now abandoned, and application Ser. No. 674,813 filed Mar. 22, 1991 (for Fluid-Control Valve System), and application Ser. No. 614,806 filed Nov. 19, 1990 (for Integral Intravenous Fluid Delivery Device), which are continuations-in-part of application Ser. No. 523,801 filed May 15, 1990 (for a Valve System with Removable Fluid Interface) now U.S. Pat. No. 5,088,515 and application Ser. No. 345,387 filed May 1, 1989, issued Dec. 11, 1990 as U.S. Pat. No. 4,976,162 (for an Enhanced Pressure Measurement Flow Control System), which is a continuation-in-part of application Ser. No. 092,481 filed Sept. 3, 1987, issued as U.S. Pat. No. 4,826,482, which is a continuation-in-part of application Ser. No. 022,167 filed Mar. 5, 1987, issued as U.S. Pat. No. 4,808,161, and application Ser. No. 836,023 filed Mar. 4, 1986, issued as U.S. Pat. No. 4,778,451. Filed concurrently herewith is an application Ser. No. 792,877 for Pump Controller using Acoustic Spectral Analysis by Kamen, Seale, Briggs and Arnold. These related applications are hereby incorporated herein by reference.

TECHNICAL FIELD

The invention relates generally to medical intravenous fluid delivery systems and more specifically to such systems that eliminate air bubbles from the intravenous fluid before it is delivered to the patient.

BACKGROUND OF THE INVENTION

It has been the object of many prior-art devices to detect the presence of air bubbles in an intravenous line. Such devices would normally set off an alarm to alert the appropriate medical personnel, who would then lightly rap the line to urge the bubbles up the line away from the patient. It is a tedious procedure to urge all the bubbles all the way up the IV line to the IV fluid reservoir. It is even more difficult to remove bubbles located downstream of a pump. Since, in an IV line that is not being pumped at high pressure, small bubbles usually do not pose much danger to the patient, busy medical personnel rarely go through the trouble of urging the bubbles all the way up the line. Consequently, the bubbles quickly move back down the line and are detected again, thereby setting off the alarm again. Thus, without an easy way of removing air from the IV line, the prior-art air-detection systems are more of a nuisance than an aid.

At least one medical apparatus in the prior art includes a line for recycling air removed from fluid back to a reservoir without opening the fluid flow loop to the environment. U.S. Pat. No. 4,874,359 to White et al. discloses a modular, power augmented medical infusion apparatus to provide rapid transfusion of relatively large quantities of blood, blood components, colloid and fluids to patients who require large quantities of these blood components to be rapidly transferred. The major components comprise a pair of filtered cardiotomy reservoirs, an air embolus sensor, a modular double roller pump, a heat exchanger, a bubble trap-filter and disposable fluid conduits. The bubble trap-filter is located in the distal most location of the recirculating loop just upstream of the Y-connector to the patient and the air sensor just downstream of the cardiotomy reservoir in the proximal location of the recirculating loop. Blood is circulated rapidly from the cardiotomy reservoir through the heat exchanger wherein it is heated or cooled as needed and through an air bubble trap filter having a nominal filtering capability of 33 microns. A secondary path from the filter is provided to permit the air trapped in the filter to be recycled to the reservoir without opening the infuser loop to the environment. The air bubble detection system uses an infra-red analyzer as a sensor. The detection system is configured to stop the pump and sound an audible alarm. It does not control the recycling of trapped air from the filter.

U.S. Pat. No. 4,764,166 to Spani discloses an ultrasonic device for detecting the presence of air in the fluid line of an IV infusion device comprises a transmitter and a receiver which are positioned to pinchingly engage a portion of the fluid line therebetween. Both the transmitter and receiver have convex-shaped lenses which contact and cause a slight indentation of the tube for enhanced coupling therebetween.

U.S. Pat. No. 4,734,269 to Clarke et al. discloses a venous reservoir bag with an integral high-efficiency bubble removal system. The system includes a container having an inlet for a fluid which includes liquid and gas bubbles, an outlet and upstream and downstream vents. A filter element is provided in the container between the inlet and the outlet. The filter element permits the passage of the liquid and inhibits the passage of the gas bubbles. The filter element is between the upstream and downstream vents so that gas bubbles can be vented through the upstream vent, and any gas bubbles downstream of the filter element can be vented through the downstream vent.

U.S. Pat. No. 4,661,097 to Fischell et al. discloses a method for removing gas bubbles from the fluid handling system of a medication infusion system implanted in a patient. Specifically, Fischell discloses a method for removing fluid and/or gas bubbles from a fluid reservoir and pumping chamber by applying a vacuum or negative pressure to the inlet filter, thereby drawing gas bubbles from the pumping chamber. The invention utilizes a fluid pump of a single valve positive displacement design with the pump chamber in fluid communication with the fluid reservoir.

None of the above references disclose a system that, on detection of air in the fluid, shuts off flow of the fluid to the patient and returns the fluid to an entry point in the system upstream of the pump.

SUMMARY OF THE INVENTION

The present invention provides an air elimination system an intravenous fluid delivery system that intravenously injects fluid into a patient. The invention may include an intravenous line with a chamber disposed therein where air may separate from the fluid. Also disposed in the intravenous line is an air detector for detecting air in the fluid and emitting a fault-condition signal, when an air bubble of a certain size is detected, or alternatively when any air bubble is detected. A return line connects the chamber to a point in the intravenous line downstream of the air detector. A pair of valves, one being disposed in the intravenous line and the other in the return line—or alternatively a single shunt valve—are employed to permit flow either (i) through the return line or (ii) to the patient. A pump is used for urging fluid through the return line when there is a fault condition. A controller receives signals from the air detector and either (i) sets the valves (or valve) to permit flow through the return line and then activates the pump, so as to move air and fluid from the air detector to the chamber, in response to a fault-condition signal, or otherwise (ii) sets the valves (or valve) so as to permit flow to the patient. The return line and the disposable portions of the pump, the air detector and the two valves may be formed in an integral device in the manner of the integral intravenous fluid delivery device disclosed in patent application Ser. No. 614,806, referenced hereinabove.

DESCRIPTION OF SPECIFIC EMBODIMENTS

The invention provides an apparatus and method for eliminating air from intravenous fluid delivery (IV) systems. In a preferred embodiment, an acoustic sensor is utilized to control the operation of valves located downstream of the IV pump so that when air bubbles are detected, an isolation valve is closed to shut off the flow of IV fluid to the patient and a purge valve is opened to return the fluid with air entrapped in it to the metering chamber.

A system according to the present invention may include an apparatus that accurately dispenses IV fluid to the patient, using sound waves both to measure fluid flow and to detect the presence of air in the IV fluid. The apparatus includes a return line that carries fluid back to the metering chamber if and when the apparatus detects air in the fluid. Although almost any air-detection system may be used, it is intended that a preferred embodiment of the present invention be used with an apparatus that uses sound waves to measure flow and uses sound waves to detect air, such as that disclosed in the above-referenced patent application for Pump Controller using Acoustic Spectral Analysis, filed concurrently with the present application.

Figure 1:
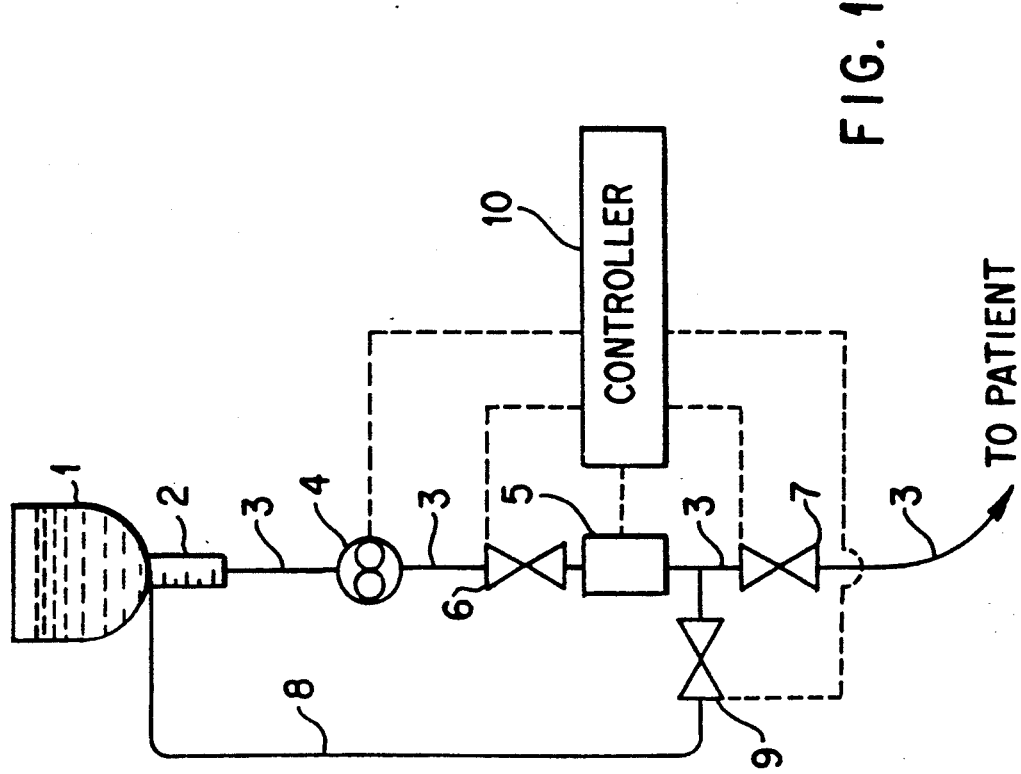
FIG. 1 is a general view of a preferred embodiment of an air elimination system according to the present invention.

FIG. 1 shows an intravenous fluid bag (or bottle) 1 and metering chamber 2, from which an intravenous line 3 provides fluid to the patient. Disposed in the line is a pump 4, an apparatus for detecting air and preferably for measuring flow rate 5, and a valve 7. The air-detection/fluid-measurement apparatus 5 is downstream of the pump 4, and the valve 7 is located downstream of the apparatus 5. The pump 4 in a preferred embodiment may be of the type disclosed in patent application Ser. No. 673,834 (for Membrane-Based Rotary Peristaltic Pump), referenced hereinabove. One end of the return line 8 is connected to the IV line 3 between the air-detection apparatus 5 and valve 7; its other end is connected to the metering chamber 2. Another valve, a purge valve 9, is located in the return line.

When air, or a certain amount of air, is detected, valve 7 is closed and purge valve 9 is opened. The pump 4 is turned on, forcing the fluid and the air bubbles in the air-detection apparatus 5 to return to the metering chamber 2. The metering chamber 2 allows the air bubbles to separate from the IV fluid. Other devices, such as a drip chamber, or even the IV bag (or bottle) 1, may be used to allow the air to separate from the fluid. When the air has been eliminated from the apparatus, purge valve 9 may be closed and the IV system may return to its normal pumping mode. A digital controller 10 receives information from the detector 5 regarding the presence of air, controls the opening and closing of valves 7 and 9, and controls the pump 4. The air detector 5, as well as the controller 10, may be made a part of a IV fluid control system, such as that disclosed in patent application Ser. No. 615,612 (for Acoustic Volume Measurement with Fluid Management Capability) and/or U.S. Pat. No. 4,976,162 (for Enhanced Pressure Measurement Flow Control System) and/or the application for Pump Controller using Acoustic Spectral Analysis filed concurrently herewith, each of which are referenced hereinabove. The system disclosed in U.S. Pat. No. 4,976,162 uses two valves, A and B, for isolating a portion of the IV fluid during a volume measurement cycle, and these are shown as valves 6 and 7 in FIG. 1; the valve B of U.S. Pat. No. 4,976,162 is used as valve 7 of the present invention. Valve 6 of the present invention corresponds valve A.

Figure 2:
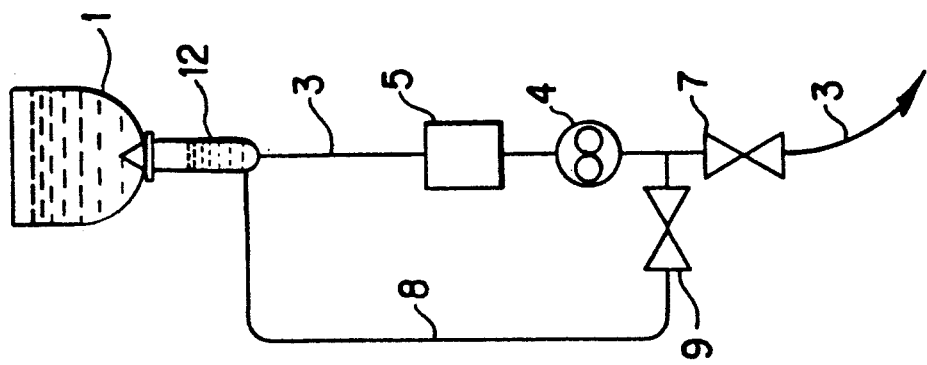
FIGS. 2 and 3 show alternative embodiments of the air elimination systems according to the present invention.
Figure 3:
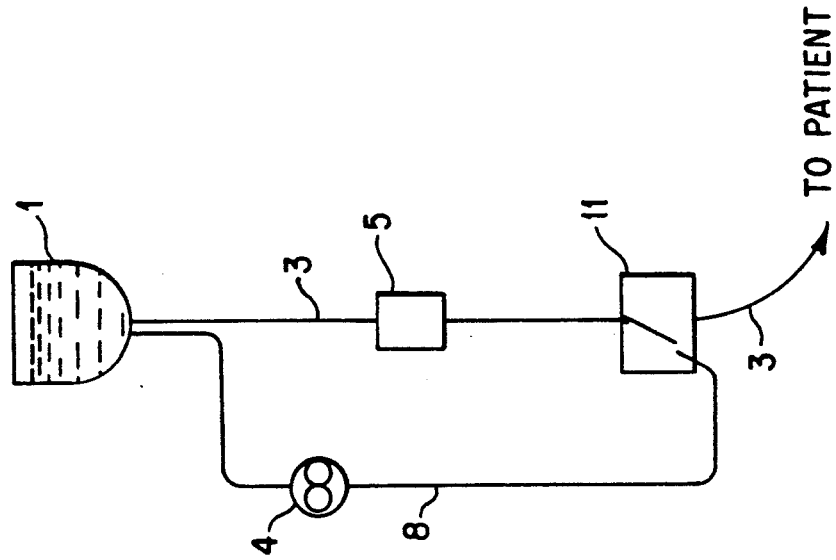

In another embodiment of the present invention the pump 4 may be located in the IV line 3 downstream of the air detector 5 but upstream of the point where the return line 8 is connected to the IV line 3, as shown in FIG. 2. The system shown in FIG. 2 has the return line returning to a simple drip chamber 12 instead of a metering chamber. FIG. 3 shows another embodiment, wherein the pump 4 is disposed in the return line 8 and the return line 8 returns fluid to the reservoir 1, and wherein a single shunt valve 11 is used instead of two separate valves 7 and 9. A disadvantage of the FIG. 3 embodiment is that the pump 4 cannot, of course, be used to pump IV fluid to the patient. Another disadvantage of the FIG. 3 embodiment is that, if any medicine has been added to the fluid in the intravenous line between the IV reservoir 1 and the shunt switch 11 just before the pump 4 is activated, that medicine may be pumped back into the IV bag 1 where it will be diluted. Therefore, any medicine should be injected into the intravenous line 3 below the shunt valve 11, if it is desired that the medicine be injected into the patient quickly.

In all the foregoing embodiments it is preferred that, when air is detected, the fluid and the air bubbles from the detector 5 is pumped back to the reservoir, metering chamber or drip chamber through the return line 8. In another embodiment the pump 4 may be reversed so that the IV fluid and air bubbles in the air detector 5 are forced up the IV line 3 back to the reservoir, with fluid in the return line 8 replenishing that which has been pumped out of the detector 5. The disadvantage of such an embodiment is that the return line 8 must be attached to the reservoir, metering chamber or drip chamber below the water-line; otherwise the pump will draw air into the return line instead of fluid, and, if the pumping continues long enough, this air will move into the IV line 3 and the air detector 5.

Figure 4:
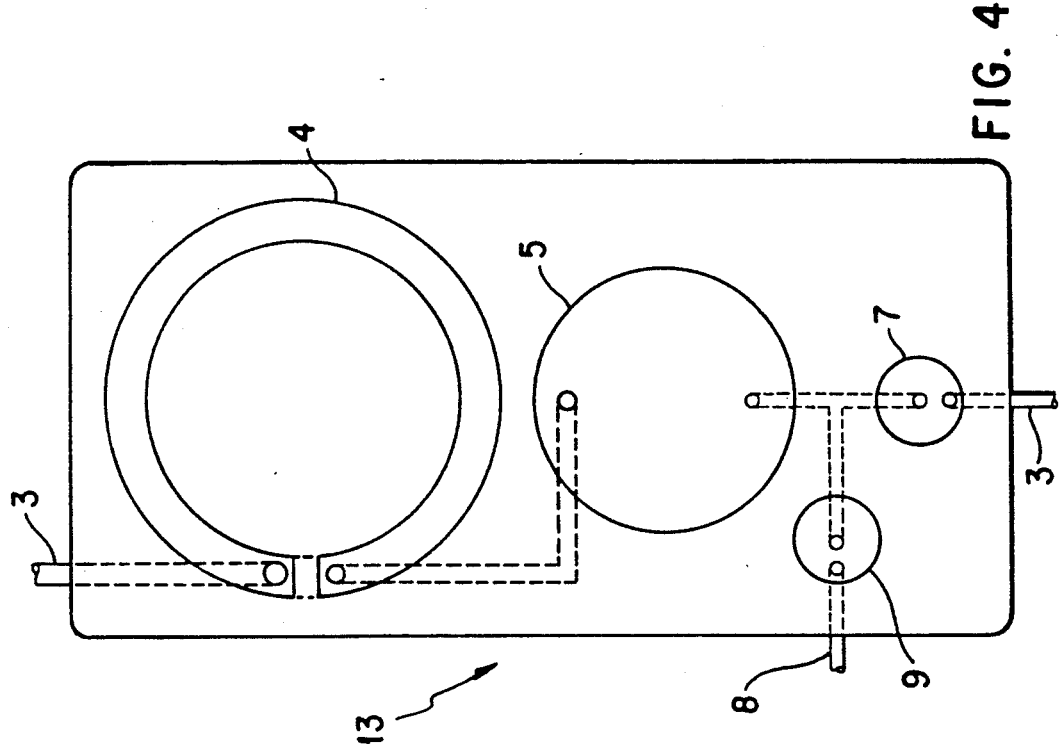
FIG. 4 shows a plan view of a disposable cassette that includes the disposable portions of a pump, an air-detection chamber and two valves, all of which are components of the system shown in FIG. 1.

FIG. 4 shows a disposable cassette 13 that may be used in the system shown in FIG. 1. The cassette 13 includes the pump 4, or more precisely the disposable portion of the pump described in patent application Ser. No. 673,834, referenced hereinabove. The valves and pressure-conduction chamber disclosed in U.S. patent application Ser. No. 523,801 (for Valve System with Removable Fluid Interface, referenced hereinabove) may be used as valves 7 and 9, and in the air detector 5. The body of the cassette 13 is made of relatively rigid material, such as a thermoplastic, and one or several flexible membranes are disposed on the rigid body to form the membranes of the valves, 7 and 9, the pressure-conduction chamber 5 and the pump 4. The flexible tube portions of the intravenous line 3 and the return line 8 are connected to the rigid portion of cassette 13, so as to communicate with the fluid passageways within the cassette 13. The disposable cassette 13 is placed into a housing that can actuate the valves 7 and s, that can detect the presence of air and/or the amount of fluid in the pressure-conduction chamber 5, and that can apply the appropriate peristaltic motion to the pump 4. Other components may be placed in this disposable cassette 13, such as a filter or an automatic shut-off valve, which are components of the cassette disclosed in application Ser. No. 614,806 (for Integral Intravenous Fluid Delivery Device, referenced hereinabove). The rotary peristaltic pump 4 may double as valve 6; when the pump is stopped, fluid is prevented from flowing through. If the peristaltic pump 4 is used also as a valve to isolate the pressure-conduction chamber during a flow-measurement cycle (as in U.S. Pat. No. 4,976,162, referenced hereinabove), it is important to stop the pump 4 at just the right position, so that when pressure is applied to the pressure-conduction chamber 5 the membrane on the pump 4 is not distended. Otherwise, the pressure-conduction chamber will not be properly isolated, and the flow rate may be improperly calculated.

Figure 5:
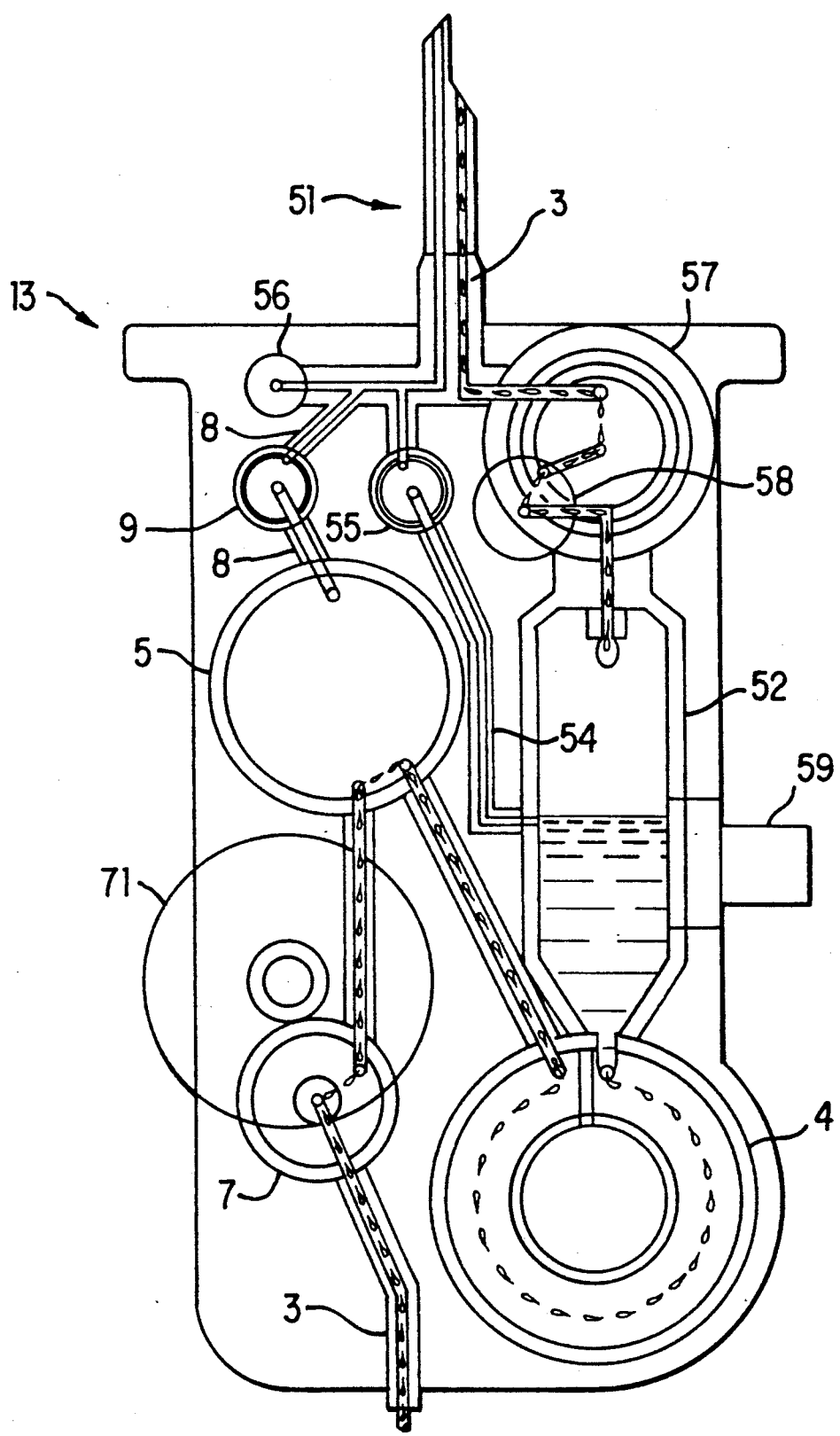
FIG. 5 shows a plan view of a disposable cassette that includes the return line and the disposable portions of a pump, an air-detection chamber and several valves.

FIG. 5 shows a disposable cassette 13 according to a preferred embodiment of the invention. This cassette 13 has a spike 51 for connecting the cassette to a fluid reservoir. Located within the spike 51 is a fluid passageway for the intravenous line 3 and another passageway for the return line 8. During normal flow the fluid flows from the fluid reservoir, through the spike 51, then to an automatic shut-off valve 57 (such as that shown in FIG. 8 of application Ser. No. 614,806, which closes automatically when the head pressure falls below a certain level), then a one-way valve 58, a drip chamber 52, a rotary peristaltic pump 4, a pressure-conduction chamber 5, and a valve 7, before passing through the intravenous line 3 to the patient. The valve 7 may be of the type shown in FIG. 7 of application Ser. No. 674,813 for Flow-Control Valve System, and may be controlled by a cam knob 71. This type of valve is useful for precisely controlling flow. A quick-disconnect valve of the type shown in application Ser. No. 748,341 (for Quick-Disconnect Valve), referenced hereinabove, may be placed in fluid communication with the drip chamber 54 or some other point along the intravenous line 3, so as to permit a secondary fluid line to be added. A return line 8 is formed as a passageway within the cassette 13 and connects the pressure-conduction chamber 5 to the fluid reservoir by passing through the spike 51. The purge valve 9 located in the return line 8 may be of the normally closed type shown in FIG. 1 of application Ser. No. 674,813. The control unit that the cassette 13 is placed in, which is also used to detect the presence of air in the pressure-conduction chamber 5, can apply pressure to the membrane of purge valve 9 so as to open it up. When air is detected in the pressure-conduction chamber 5, the control unit opens purge valve 9, closes valve 7 by turning the cam knob 71 and creates the rotary peristaltic motion for pump 5, so that the air in the pressure-conduction chamber 5 is urged through the return line 8 up to the fluid reservoir.

The cassette 13 shown in FIG. 5 has several other features. A feature, useful when the cassette 51 is attached a rigid IV bottle, is the one-way valve 56 which connects the return line 8 to the atmosphere; this one-way valve 56 permits air to pass through the spike 51 to replace the fluid that has left the IV bottle, which is not able to collapse like an IV bag when fluid leaves it. The cassette 13 of FIG. 5 also has a priming passageway 54, which is used to prime the drip chamber 52. Located in the priming passageway 54 is a normally closed valve 55, which may be of the type shown in FIG. 1 of application Ser. No. 674,813. In order to prime the drip chamber 52, valve 55 may be held open while the pressure-conduction chamber 5 is repeatedly squeezed. Using this structure and this procedure, wherein the priming passageway 54 is attached midway up on the drip chamber 52, and a one-way valve 58 placed in the intravenous line 3 between the reservoir and the drip chamber, prevents the drip chamber from being over-primed.

The cassette 13 is preferably made of a clear, thermoplastic material, so that medical personnel may view the fluid dripping in the drip chamber 52, or so that the cassette may be placed in a control unit that measures flow rate by counting drips.

What is claimed is:

1. An air elimination system, for an intravenous fluid delivery system for intravenous injection of fluid into a patient, comprising:
    an intravenous line;
    separation means for permitting the separation of air from the fluid;
    air-detection means, disposed in the intravenous line, for detecting air in the fluid, and emitting a fault-condition signal;
    a return line connecting the separation means to a point in the intravenous line downstream of the air-detection means;
    valve means, disposed in the intravenous line and return line, for permitting (i) flow through the return line or (ii) to the patient;
    pump means for urging fluid through the return line upon activation; and
    control means, in communication with the air-detection means, for (i) setting the valve means to permit flow through the return line and activating the pump means, so as to move air and fluid from the air-detection means to the separation means, in response to a fault-condition signal, and otherwise (ii) setting the valve means to permit flow to the patient.

2. A system according to claim 1, wherein the air-detection means includes flow-measurement means for measuring fluid flow rate.

3. A system according to claim 1, wherein the pump means includes a pump disposed in the intravenous line upstream from the valve means.

4. A system according to claim 1, wherein the separation means includes a metering chamber.

5. A system according to claim 1, wherein the separation means includes a drip chamber.

6. A system according to claim 1, wherein portions of the air-detection means, the valve means and the pump means are formed in an integral device.

7. A system according to claim 1, wherein the separation means includes an intravenous fluid reservoir.

8. A system according to claim 7, wherein the return line and portions of the air-detection means, the valve means and the pump means are formed in an integral device.

9. A method for eliminating air from an intravenous fluid delivery system, having a chamber where air may separate from the fluid, a pump, an intravenous line and an air detector, comprising the steps of:

detecting air in the fluid;

emitting a signal when a specified amount of air is detected in the fluid;

providing a first valve in the intravenous line;

providing a return line from a point in the intravenous line between the pump and the first valve;

providing a second valve in the return line;

closing the first valve in response to the signal;

opening the second valve in response to the signal; and using the pump to urge fluid through the return line to the chamber in response to the signal.

10. A method according to claim 9, further including the step of providing an intravenous fluid reservoir as the chamber.

11. A method according to claim 9, wherein the step of emitting a signal is performed when any air is detected in the fluid.

12. A system according to claim 6, wherein the pump means includes a pump disposed in the intravenous line upstream from the valve means.

13. A system according to claim 7, wherein the pump means includes a pump disposed in the intravenous line upstream from the valve means.

14. A system according to claim 8, wherein the pump means includes a pump disposed in the intravenous line upstream from the valve means.

* * * * *